(12) United States Patent
Kim et al.

(10) Patent No.: US 10,638,943 B2
(45) Date of Patent: May 5, 2020

(54) APPARATUS AND METHOD OF MONITORING BIOSIGNAL OF CYCLIST AND COMPUTER READABLE RECORDING MEDIUM

(71) Applicant: Industry-Academic Cooperation Foundation, Chosun University, Gwangju (KR)

(72) Inventors: Youn Tae Kim, Daejeon (KR); Jae Hyo Jung, Gwangju (KR); Si Ho Shin, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 189 days.

(21) Appl. No.: 15/871,334

(22) Filed: Jan. 15, 2018

(65) Prior Publication Data

US 2019/0104955 A1    Apr. 11, 2019

(30) Foreign Application Priority Data

Oct. 11, 2017  (KR) .................. 10-2017-0129840

(51) Int. Cl.
| | | |
|---|---|---|
| *A61B 5/0488* | (2006.01) | |
| *A61B 5/0245* | (2006.01) | |
| *A61B 5/00* | (2006.01) | |
| *A61B 5/0472* | (2006.01) | |
| *A61B 5/0452* | (2006.01) | |
| *B62J 99/00* | (2020.01) | |

(52) U.S. Cl.
CPC ........ *A61B 5/02455* (2013.01); *A61B 5/0452* (2013.01); *A61B 5/0472* (2013.01); *A61B 5/0488* (2013.01); *A61B 5/4519* (2013.01); *A61B 5/6895* (2013.01); *A61B 5/7257* (2013.01); *A61B 2503/10* (2013.01); *B62J 2099/002* (2013.01); *B62K 2207/00* (2013.01)

(58) Field of Classification Search
CPC .............. A61B 5/0488; A61B 5/04012; B62K 2207/00; B62J 2099/002
See application file for complete search history.

(56) References Cited

U.S. PATENT DOCUMENTS

| | | | | |
|---|---|---|---|---|
| 5,361,775 A | * | 11/1994 | Remes | ............... A61B 5/04012 600/546 |
| 7,764,990 B2 | * | 7/2010 | Martikka | ............. A61B 5/0488 600/520 |
| 2016/0263439 A1 | * | 9/2016 | Ackland | ............. G06F 19/3481 |
| 2019/0183412 A1 | * | 6/2019 | Huijbregts | ........... A61B 5/0205 |

FOREIGN PATENT DOCUMENTS

| | | |
|---|---|---|
| KR | 10-2000-0072178 A | 12/2000 |
| KR | 10-2017-0056396 A | 5/2017 |
| KR | 10-2017-0129840 A | 5/2017 |

* cited by examiner

*Primary Examiner* — George R Evanisko
(74) *Attorney, Agent, or Firm* — Renner, Otto, Boisselle & Sklar, LLP (57) ABSTRACT

An apparatus for monitoring a biosignal of a cyclist includes an electrocardiogram measuring sensor measuring an electrocardiogram signal of a cyclist, an electromyogram measuring sensor measuring an electromyogram signal of the cyclist, and a determination module determining muscle fatigue of the cyclist, based on at least one of a change in a heart rate of the measured electrocardiogram signal and a change in a frequency component of the measured electromyogram signal.

13 Claims, 13 Drawing Sheets

APPARATUS AND METHOD OF MONITORING BIOSIGNAL OF CYCLIST AND COMPUTER READABLE RECORDING MEDIUM

CROSS-REFERENCE TO RELATED APPLICATION(S)

This application claims benefit of priority to Korean Patent Application No. 10-2017-0129840 filed on Oct. 11, 2017 in the Korean Intellectual Property Office, the disclosure of which is incorporated herein by reference in its entirety.

BACKGROUND

1. Field

The present disclosure relates to an apparatus and method of monitoring a biosignal of a cyclist, and a computer readable recording medium.

The present disclosure arises from research supported by the Basic Science Research Program through the National Research Foundation of Korea (NRF) funded by the Ministry of Education (No. 2018R1A 6A1A 030 15496) and the Mid-career Researcher Program (No. 2016R1A2B3009423) through a NRF grant funded by the Ministry of Science and ICT of Korea (MSIT).

2. Description of Related Art

Environmental pollution and resource depletion due to the continuous increase in the use of cars are becoming serious problems in the international community. With such phenomena, modern individuals are increasingly using electric kickboards, bicycles, and the like.

The tracking of bicycles is being carried out in various ways, such as monitoring the exertion of a cyclist, GPS ride tracking, the prevention of bicycle theft, and the like, through the convergence of various transportation and IT technologies. Thus, bicycles have become a convenient means of transportation and a useful type of exercise equipment for people of all ages. However, in the case that a cyclist rides a bicycle strenuously, the user's cardiovascular system and muscles may be seriously damaged.

In the case of cyclist monitoring applications according to the related art, since only data such as pulse, position information, and calorie consumption are provided, an accident may occur due to injuries such as cardiac arrest or muscle spasms due to excessive exercise.

SUMMARY

An aspect of the present disclosure is to provide an apparatus and method of monitoring a biosignal of a cyclist, capable of preventing the occurrence of an accident due to an injury such as cardiac arrest or muscle cramps due to excessive exercise, and a computer-readable recording medium.

According to an aspect of the present disclosure, an apparatus for monitoring a biosignal of a cyclist includes an electrocardiogram measuring sensor measuring an electrocardiogram signal of a cyclist, an electromyogram measuring sensor measuring an electromyogram signal of the cyclist, and a determination module determining muscle fatigue of the cyclist, based on at least one of a change in a heart rate of the measured electrocardiogram signal and a change in a frequency component of the measured electromyogram signal.

According to an aspect of the present disclosure, a method of monitoring a biosignal of a cyclist includes a first operation of measuring an electrocardiogram signal of a cyclist by an electrocardiogram measuring sensor, a second operation of measuring an electromyogram signal of the cyclist by an electromyogram measuring sensor, and a third operation of determining a degree of muscle fatigue of the cyclist, by a determination unit, based on at least one of a change in a heart rate of the measured electrocardiogram signal and a change in a frequency component of the measured electromyogram signal.

According to an aspect of the present disclosure, there is a recording medium, on which a program for execution of the method of monitoring a biosignal of a cyclist, described above is recorded.

BRIEF DESCRIPTION OF DRAWINGS

The above and other aspects, features, and advantages of the present disclosure will be more clearly understood from the following detailed description, taken in conjunction with the accompanying drawings, in which.

DETAILED DESCRIPTION

Hereinafter, embodiments in the present disclosure are described in detail with reference to the accompanying drawings. However, exemplary embodiments in the present disclosure may be variously modified, and the scope of the present invention is not limited to exemplary embodiments described below. The shape and size of elements in the drawings may be exaggerated for clarity, and elements denoted by the same reference numerals throughout the drawings are referred to the same elements.

Figure 1:
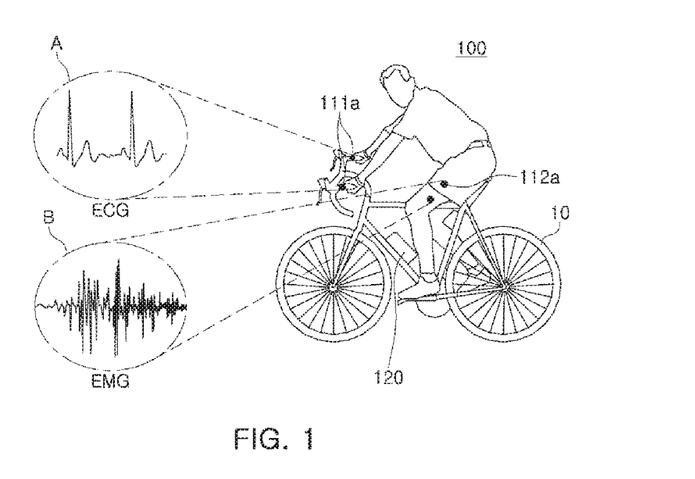
FIG. 1 is a drawing illustrating a position of an apparatus for monitoring a biosignal of a cyclist according to an exemplary embodiment in the present disclosure.
Figure 2:
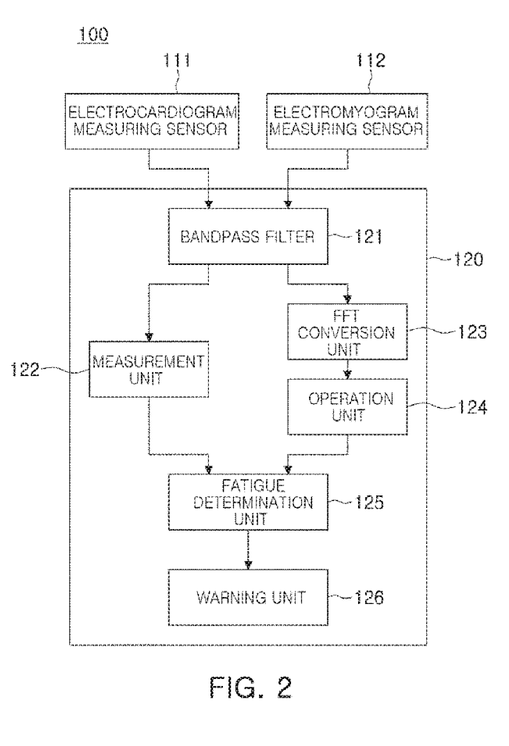
FIG. 2 is a block diagram illustrating an internal configuration of a determination module according to an exemplary embodiment in the present disclosure.

FIG. 1 is a drawing illustrating a position of an apparatus for monitoring a biosignal of a cyclist according to an exemplary embodiment. FIG. 2 is a block diagram illustrating an internal configuration of a determination module according to an exemplary embodiment.

As illustrated in FIGS. 1 and 2, an apparatus 100 for monitoring a biosignal of a cyclist according to an exemplary embodiment may include an electrocardiogram measuring sensor 111 including an electrode 111a for measuring an electrocardiogram signal of a cyclist, an electromyogram measuring sensor 112 including an electrode 112a for measuring an EMG signal of the cyclist, and a determination module 120 for determining muscle fatigue of the cyclist, based on at least one of a change in a heart rate of a measured electrocardiogram signal and a change in frequency components of a measured EMG signal.

With reference to FIG. 2, the determination module 120 may be configured to include a bandpass filter 121, a measurement unit 122, a fast fourier transform (FFT) conversion unit 123, an operation unit 124, a fatigue determination unit 125, and a warning unit 126.

The electrocardiogram measuring sensor 111 may measure an electrocardiogram (ECG) signal of a cyclist, as illustrated by reference character A of FIG. 1, and may transmit the measured electrocardiogram signal to the band pass filter 121.

To this end, the electrode 111a of the electrocardiogram measuring sensor 111 may be a dry electrode attached to a handlebar of a bicycle. Such an electrode may be generally divided into one of a wet electrode or a dry electrode. The wet electrode is disposable, and may not be suitable for use on a bicycle handlebar since the electrode is coated with conductive gel, while the dry electrode is reusable and does not require conductive gel, and thus, may be suitable for use on a bicycle handlebar. Electrocardiogram signals may be measured from the palm of the hand when a bicycle handlebar, provided with the electrode 111a, a dry electrode, is held with both hands of a cyclist.

The electromyogram (EMG) sensor 112 may measure an EMG signal of a cyclist, as illustrated in reference character B of FIG. 1, and may transmit the measured EMG signal to the bandpass filter 121. In the case of the EMG signal, as muscle fatigue accumulates, a high frequency component may decrease and a low frequency component may increase. In an exemplary embodiment, muscle fatigue may be determined using this principle.

In order to determine muscle fatigue, the electrode 112a of the electromyogram measuring sensor 112 may be attached to a thigh of the cyclist. The cyclist's thigh described above is merely an example for facilitating understanding of the present disclosure, and the electrode 112a may be attached to any other body part, such as a calf, or the like. In addition, the electrode 112a of the electromyography measuring sensor 112 may be a Carbon NanoTube (CNT) composite electrode, a detailed structure of which will be described below with reference to FIGS. 7A to 10.

The bandpass filter 121 may remove frequencies other than a frequency band of a heart rate of a measured electrocardiogram signal and a frequency band of an EMG signal. The electrocardiogram signal, having passed through the bandpass filter 121, may be transmitted to the measurement unit 122, and the EMG signal, having passed through the bandpass filter 121, may be transmitted to the FFT conversion unit 123.

The measurement unit 122 may measure the heart rate based on a QRS wave or a P wave of the electrocardiogram signal. The measured heart rate may be transmitted to the fatigue determination unit 125. Hereinafter, a process of measuring the heart rate based on the QRS wave will be described with reference to FIG. 3.

Figure 3:
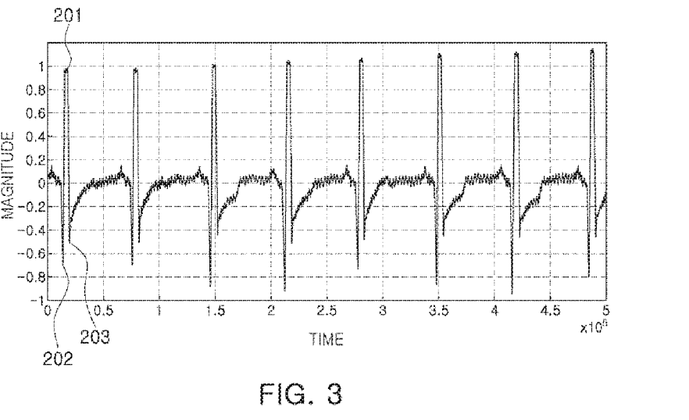
FIG. 3 is a diagram illustrating a QRS wave of an electrocardiogram signal according to an exemplary embodiment in the present disclosure.

In detail, FIG. 3 is a diagram illustrating a QRS wave of an electrocardiogram signal according to an exemplary embodiment.

As illustrated in FIG. 3, a Q wave 202 of the electrocardiogram signal may have a negative (−) peak value present in a lowermost portion in the electrocardiogram signals, and an R wave 201 thereof may have a positive (+) peak value present in an uppermost portion in the electrocardiogram signals. Thus, each threshold value thereof may be set to detect a component exceeding or not exceeding the threshold value, as the Q wave or the R wave of the electrocardiogram signal. On the other hand, since an S wave 203 indicates a magnitude of −0.4 to −0.6 of the electrocardiogram signal, the S wave 203 may be detected by setting a negative (−) peak value present in the range of the magnitude of −0.4 to −0.6 to be the S wave. The Q, R and S waves may be respectively detected and may be simultaneously output in the graph, and three components of the QRS waves may be determined as one heart rate. Separately therefrom, for example, when a P wave is detected, based on a P wave (not shown), the detected P wave may be determined as being one heart rate.

Subsequently, the fatigue determination unit 125 may determine muscle fatigue of the cyclist based on the heart rate transmitted from the measurement unit 122. A determination result thereof may be transmitted to the warning unit 126.

In detail, for example, when the heart rate transmitted by the measurement unit 122 is equal to or greater than a preset threshold value, the fatigue determination unit 125 may determine that fatigue has accumulated in the muscles.

In this case, the preset threshold value may be, for example, (220—cyclist's age) beats per minute (BPM), and the fatigue determination unit 125 may determine that, when a heart rate equal to or greater than (220—cyclist's age) BPM is maintained for a predetermined period of time, the cyclist is exercising, putting burden on the heart of the cyclist.

On the other hand, the EMG signal having passed through the bandpass filter 121 may be transmitted to the FFT conversion unit 123, and the FFT conversion unit 123 may perform FFT conversion on the measured EMG signal. The FFT-converted EMG signal may be transmitted to the operation unit 124.

The operation unit 124 may obtain at least one of an intermediate frequency and an average frequency of the FFT-converted EMG signal, and may transmit the obtained at least one of the intermediate frequency and the average frequency to the fatigue determination unit 125.

The fatigue determination unit 125 may determine a degree of muscle fatigue of the cyclist, based on the at least one of an intermediate frequency and an average frequency transmitted from the operation unit 124. A determination result thereof may be transmitted to the warning unit 126.

Figure 4:
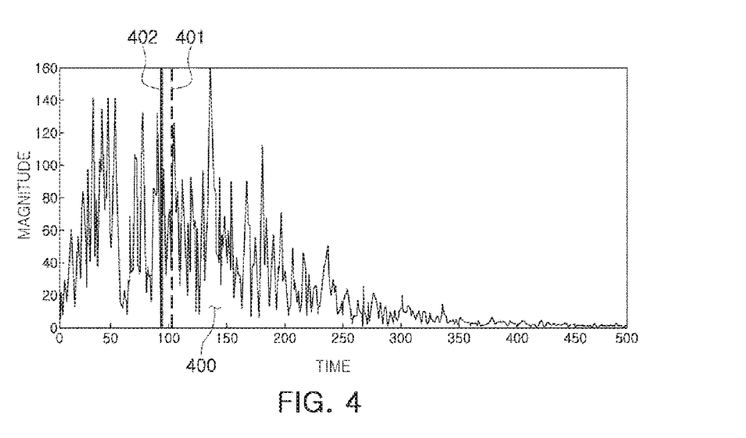
FIG. 4 illustrates an intermediate frequency and an average frequency of an electromyogram signal according to an exemplary embodiment in the present disclosure.

In this regard, FIG. 4 illustrates an intermediate frequency and an average frequency of an EMG signal according to an exemplary embodiment.

As illustrated in FIG. 4, an intermediate frequency 402 of the EMG signal may be a frequency at a point obtained by dividing an area 400 of an FFT-converted EMG signal in half, and an average frequency 401 of the EMG signal described above may be a frequency at a point representing an average value of the area 400 of the FFT-converted EMG signal.

As described above, in the case of the EMG signal, as the muscle fatigue accumulates, a high frequency component may decrease, and a lower frequency component may increase. In an exemplary embodiment of the present disclosure, the muscle fatigue may be determined using this principle.

To this end, for example, when the obtained intermediate frequency 402 is lower than a first threshold frequency or the obtained average frequency 401 is lower than a preset second threshold frequency, the fatigue determination unit 125 according to an exemplary embodiment may determine that fatigue has accumulated in the muscles.

In this case, the first threshold frequency or the second threshold frequency may have a value of approximately 60 Hz or less, and both may have the same value or different values, that may be changeable values depending on a cyclist. Thus, the first threshold frequency or the second threshold frequency is not specified by a specific value in the exemplary embodiments of the present disclosure.

FIGS. 5A to 5D are diagrams illustrating a change in muscle fatigue due to continuous exercise of a cyclist.

Figure 5A:
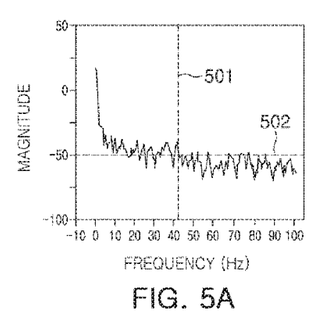
FIGS. 5A to 5D are diagrams illustrating a change in muscle fatigue due to continuous exercise of a cyclist.
Figure 5B:
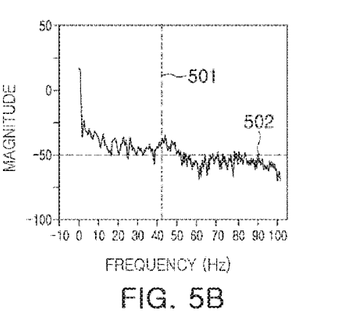
Figure 5C:
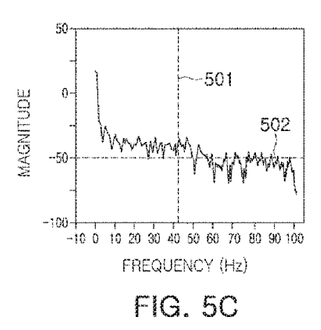
Figure 5D:
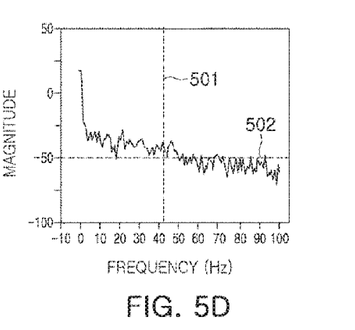

In detail, FIGS. 5A to 5D illustrate magnitudes of respective frequency components. FIG. 5A illustrates a magnitude of a frequency component before exercise, FIG. 5B illustrates a magnitude of a frequency component at a point in time after 10 minutes have passed from the start of exercise, FIG. 5C illustrates a magnitude of a frequency component at a point in time after 20 minutes have passed from the start of exercise, and FIG. 5D illustrates a magnitude of a frequency component at a point in time after 30 minutes have passed from the start of exercise, in which straight lines 501 and 502 are added with respect to the same frequency and the same magnitude in the drawings, to observe a change in low frequency components.

As illustrated in FIGS. 5A to 5D, the magnitude of low-frequency components may gradually increase as the exercise duration time increases.

In an ultimate operation, the warning unit 126 may alert the cyclist using at least one of acoustic and visual methods according to a determination result transmitted from the fatigue determination unit 125.

As described above, according to an exemplary embodiment, an accident may be prevented from occurring due to injuries such as cardiac arrest or muscle spasms due to excessive exercise by determining muscle fatigue based on ECG and EMG of a cyclist.

The electrode 112a of the electromyography measuring sensor 112 may be a CNT composite electrode. Hereinafter, a detailed structure of the CNT composite electrode will be described with reference to FIGS. 7A to 10.

FIGS. 7A to 7F are views illustrating a CNT composite electrode 700 using vacuum suction, according to an exemplary embodiment.

Figure 7A:
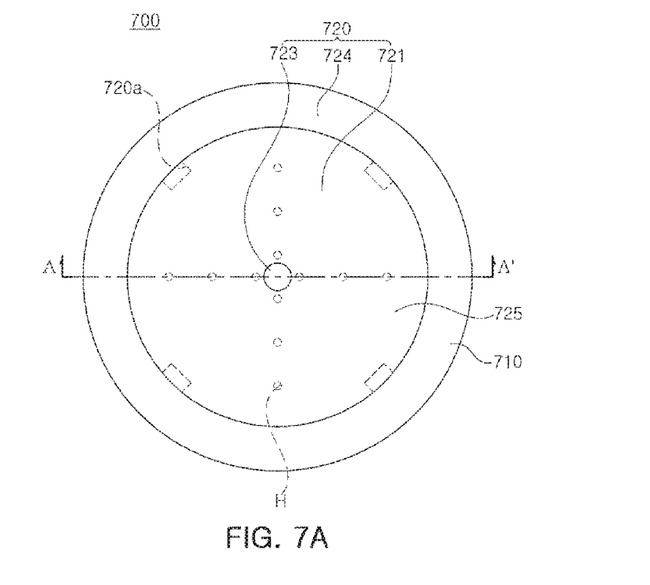
FIGS. 7A to 7F are views illustrating a Carbon NanoTube (CNT) composite electrode using vacuum suction according to an exemplary embodiment in the present disclosure.
Figure 7B:
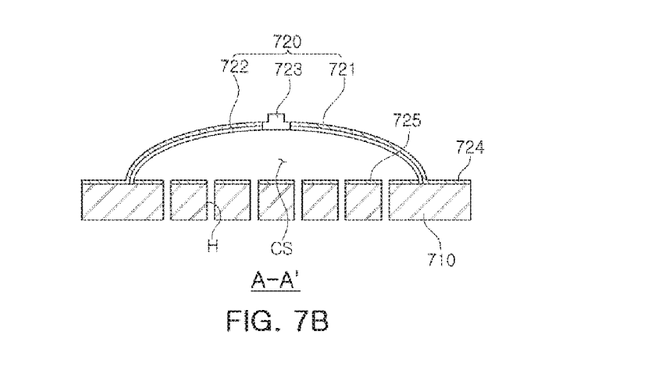
Figure 7C:
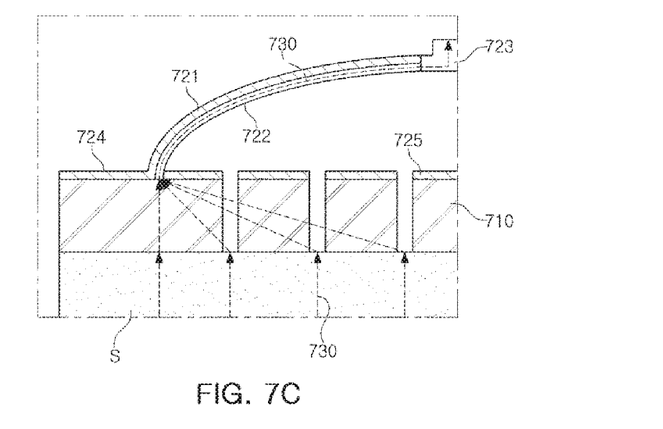
Figure 7D:
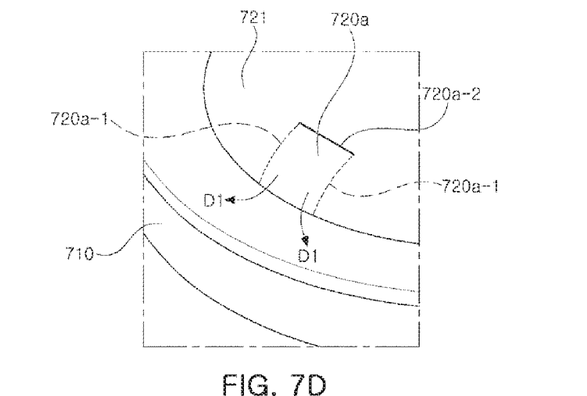
Figure 7E:
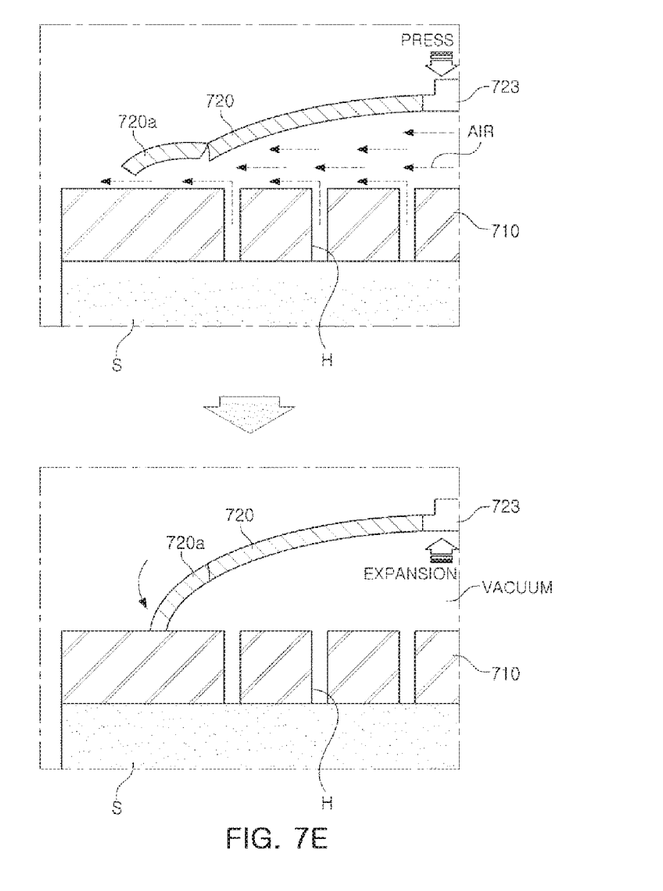
Figure 7F:
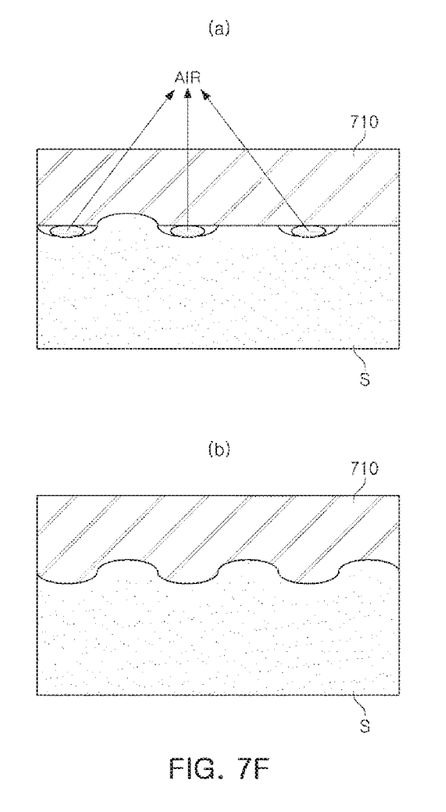

In detail, FIG. 7A is a plan view of the CNT composite electrode according to an exemplary embodiment, when viewed above, FIG. 7B is a cross-sectional view taken along line A-A' of FIG. 7A, FIG. 7C is a drawing illustrating a biosignal transmission process by the CNT composite electrode according to an exemplary embodiment, FIG. 7D is a view of an air discharge portion formed in an upper electrode of FIG. 7A, FIG. 7E provides views illustrating operations of the air discharge portion of FIG. 7D, and FIG. 7F provides views illustrating an adhesion state of a subject body depending on a material of a lower electrode in a CNT composite electrode according to an exemplary embodiment. In this case, the subject body may be a portion such as the thigh of a cyclist.

As illustrated in FIGS. 7A and 7B, the CNT composite electrode 700 using vacuum suction, according to an exemplary embodiment, may include a lower electrode 710 and an upper electrode 720.

The lower electrode 710 may be configured to include a plurality of through holes H to allow air between skin S, of the body of the subject, and the electrodes 710 and 720, to be removed, and may be attached to the skin S of the body of the subject to detect a biosignal.

The lower electrode 710 may be formed of a material having adhesiveness and conductivity, and may be a circular plate-shaped structure connected to a conductive layer 722 of the upper electrode 720 to be described later. Although the shape of the lower electrode 710 described above is illustrated as being a circular shape, various shapes such as a quadrangular shape or the like may be employed.

The material having the adhesiveness and conductivity may include a mixed material of Carbon NanoTubes (CNT) and adhesive polydimethylsiloxane (aPDMS).

FIG. 7F provides views illustrating an adhesion state of the skin S of the subject body depending on a material of the lower electrode 710 in the CNT composite electrode according to an exemplary embodiment, (a) of FIG. 7F illustrates a case in which the material of the lower electrode 710 is silicon, and (b) of FIG. 7F illustrates a case in which the material of the lower electrode 710 is aPDMS.

As illustrated in FIG. 7F, for example, when the lower electrode 710 is formed of aPDMS, a space between the lower electrode 710 and the skin may be significantly reduced, thereby increasing adhesion between the lower and upper electrodes 710 and 720 and the skin S of the subject body.

Referring again to FIGS. 7A and 7B, the upper electrode 720 may be provided on one surface of the lower electrode 710 to form a closed space CS between the upper electrode 720 and the lower electrode 710, and may be configured to receive a biosignal detected by the lower electrode 720.

The upper electrode 720 may include an arcuate structure 721 formed of a material having elastic force and restoring force, a conductive layer 722 configured to be formed on an internal surface of the arcuate structure 721, and a snap connector 723 disposed on an external surface of the arcuate structure 721 and configured to penetrate through the arcuate structure 721 to be connected to the conductive layer 722. In this case, the material of the arcuate structure 721 having elastic force and restoring force may include, for example, silicon.

The conductive layer 722 may include a conductor, coated using sputtering, or attached in the form of a conductive wire or a conductive tape, on the entirety or a portion of the internal surface of the arcuate structure 721. The conductive layer 722 may be connected to the snap connector 723 and the lower electrode 710.

The snap connector 723 may be used to transmit a biosignal externally, and may be formed of a metal. The snap connector 723 may be in the form of a button for use in general wet Ag/AgCl electrodes.

According to an exemplary embodiment, on one surface of the circular plate-shaped structure 710, for example, the lower electrode 710, an insulation layer 725 may be further formed to prevent contact between the conductive layer 722 of the upper electrode 720 and the circular plate-shaped structure 710 by external force. For example, if the conductive layer 722 of the upper electrode 720 and the circular plate-shaped structure 710 come into contact with each other due to applied external force, distortion and noise of the biosignal may be introduced.

In addition, an insulating layer 724 may further be formed on one surface of the circular plate-shaped structure 710 to which the arcuate structure 721 is not attached, to prevent noise from an external environment by covering an exposed portion of the circular plate-shaped structure 710.

FIG. 7C is a view illustrating a biosignal transmission process by a CNT composite electrode according to an exemplary embodiment.

As illustrated in FIG. 7C, a biosignal 730 of the skin S of the subject body may be transmitted to the snap connector 723, through the lower electrode 710 and the conductive layer 722 formed on an internal surface of the arcuate structure 721 of the upper electrode.

According to an exemplary embodiment, the upper electrode 720 may include an air discharge portion 720a configured to allow the upper electrode 720 and the lower electrode 710 to be attached to the skin S of the subject body via vacuum suction by discharging air present in the closed space CS and the through hole H externally. The air discharge portion 720a described above may be provided as at least two or more air discharge portions as illustrated in FIG. 7A.

The air discharge portion 720a described above is illustrated in FIG. 7D.

Referring to FIG. 7D, the air discharge portion 720a may have a hinge structure. For example, the air discharge portion 720a may correspond to a portion of the arcuate structure 721, may include cutting portions 720a-1 formed on both sides thereof to be parallel to each other, and may be opened in an external direction D1, based on a hinged portion 720a-2 which is not cut, to be restored. The air discharge portion 720a may be formed on one side of the arcuate structure 721 in contact with the circular plate-shaped structure 710, in such a manner that the air discharge portion 720a is opened in the external direction D1 when external force is applied, and is restored to an original state when the external force is removed.

FIG. 7E illustrates an operational principle of the air discharge portion 720a according to the exemplary embodiment described above.

As illustrated in FIG. 7E, for example, when external force is applied and the upper electrode 720, in detail, the snap connector 723, is pressed, the air discharge portion 720a may be opened and the air in the closed space CS (see FIG. 7B) may be discharged externally through the opened air discharge portion 720a. Then, when the external force is removed, the air discharge portion 720a may be restored to an original state, to allow the inside of the closed space CS (see FIG. 7B) to form a vacuum, such that the upper electrode 720 and the lower electrode 710 may be attached to the skin S of the body of the subject via vacuum suction.

Figure 8A:
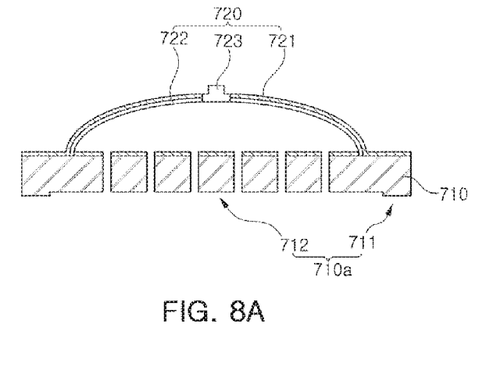
FIGS. 8A and 8B are views illustrating an air discharge portion formed on a lower electrode, and an operational principle of the air discharge portion, according to another exemplary embodiment in the present disclosure.
Figure 8B:
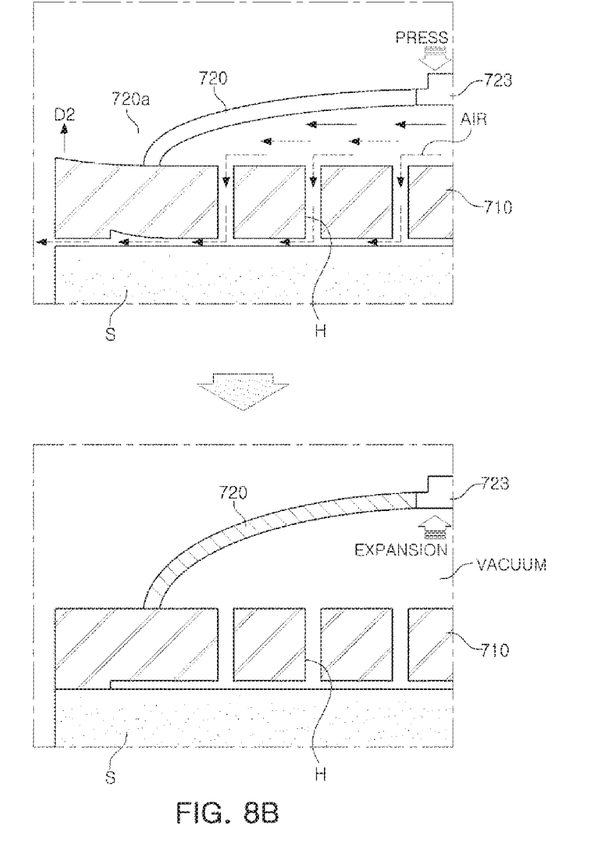

FIGS. 8A and 8B are views illustrating an air discharge portion formed on a lower electrode, and an operational principle of the air discharge portion, according to another exemplary embodiment.

In a manner different from the exemplary embodiment of FIG. 7A, an air discharge portion 710a illustrated in FIG. 8A may be configured to be disposed on a lower electrode 710.

In detail, the air discharge portion 710a may be formed on one surface, for example, a lower surface, of a circular plate-shaped structure 710 adhered to the skin S of the body of the subject, and may include an outer frame portion 711 formed to protrude and a central portion 712 formed to be concave.

The air discharge portion 710a according to the exemplary embodiment described above may operate as illustrated in FIG. 8B.

In detail, as illustrated in FIG. 8B, for example, when an upper electrode 720 has external force applied thereto, the outer frame portion 711 of the lower electrode 710 may be lifted in an upward direction D2, and air inside the closed space CS of FIG. 7B may be discharged externally. Then, when the external force is removed, the outer frame portion 711 of the lower electrode 710 may be restored to the original state to allow the inside of the closed space CS (FIG. 7B) to form a vacuum, such that the upper electrode 720 and the lower electrode 710 may be attached on the skin S of the body of the subject via vacuum suction.

Figure 9A:
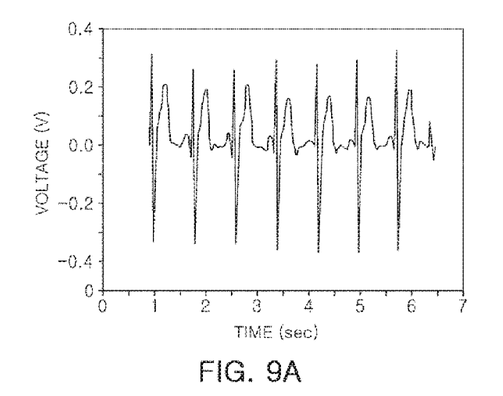
FIGS. 9A and 9B are examples of biosignals measured using a wet electrode of the related art and a CNT composite electrode according to an exemplary embodiment in the present disclosure.
Figure 9B:
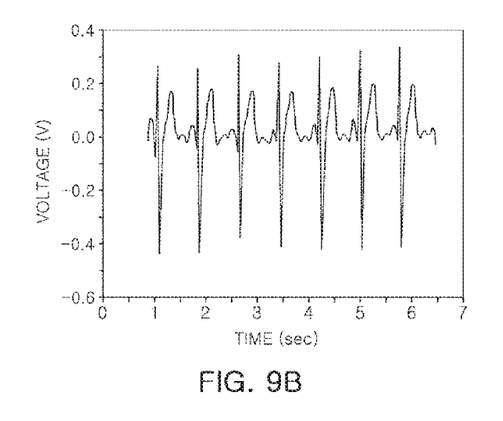

FIGS. 9A and 9B are examples of biosignals measured using a wet electrode of the related art and a CNT composite electrode according to an exemplary embodiment in the present disclosure. FIG. 9A illustrates a biosignal measured using a commercialized wet electrode, and FIG. 9B illustrates a biosignal measured using a CNT composite electrode according to an exemplary embodiment.

As illustrated in FIGS. 9A and 9B, it can be seen that there is no large difference between the biosignals measured in an existing commercialized wet electrode of the related art and the CNT composite electrode according to an exemplary embodiment in the present disclosure. Thus, it can be seen that the CNT composite electrode may be utilized as a biosignal electrode according to an exemplary embodiment.

Figure 10:
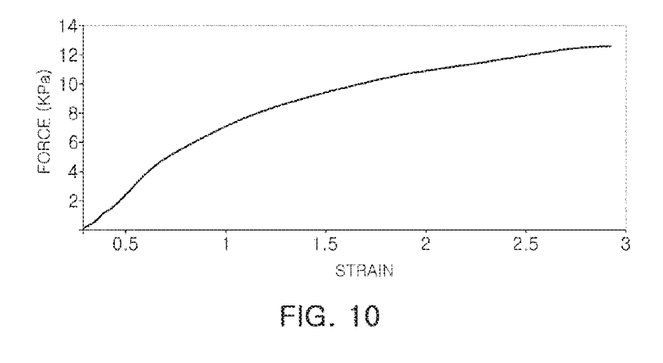
FIG. 10 is a drawing illustrating data obtained by measuring force that may be exerted when a CNT composite electrode, according to an exemplary embodiment, is lifted vertically using a tensioner in a state in which the CNT composite electrode is attached to a subject body.

FIG. 10 is a drawing illustrating data obtained by measuring force that may be exerted when the CNT composite electrode, according to an exemplary embodiment, is lifted vertically using a tensioner in a state in which the CNT composite electrode is attached to a subject body.

As illustrated in FIG. 10, the CNT composite electrode according to an exemplary embodiment may hold up to 12 kPa, such that a biosignal may be accurately measured without dropping of an electrode, even during strenuous exercise.

As described above, by attaching the electrode to the skin of the subject via vacuum suction, the electrode may be attached to the skin of the subject without using any other tool or adhesive.

In addition, according to an exemplary embodiment, as the lower electrode includes a material of aPDMS, a space due to wrinkles in the skin of the subject may be significantly reduced, thereby maintaining adhesion force of the electrode and preventing skin troubles that may occur during elongated measurement.

Figure 6:
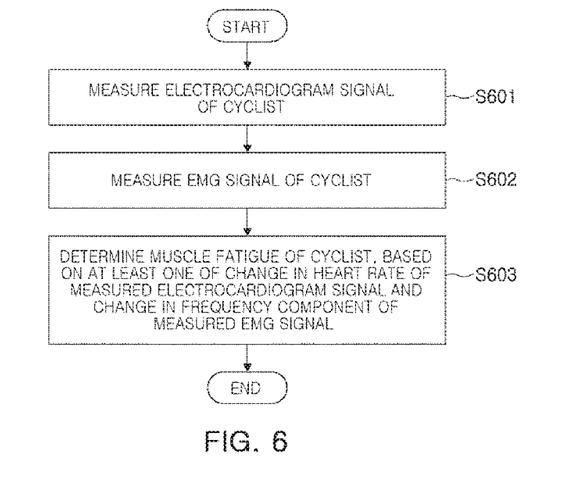
FIG. 6 is a flowchart illustrating a method of monitoring a biosignal of a cyclist according to an exemplary embodiment in the present disclosure.

FIG. 6 is a flowchart illustrating a method of monitoring a biosignal of a cyclist according to an exemplary embodiment. Descriptions overlapped with those with reference to FIGS. 1 to 5 will be omitted.

As illustrated in FIG. 6, an electrocardiogram measuring sensor 111 may measure an electrocardiogram signal of a cyclist in S601. The measured electrocardiogram signal may be transmitted to a determination module 120.

Subsequently, an EMG measurement sensor may measure an EMG signal of the cyclist in S602. The measured EMG signal may be transmitted to the determination module 120.

Although the measurement of the electrocardiogram signal and the EMG signal has been described above in the order of measurement of the electrocardiogram signal and the EMG signal, the order of measurement thereof may be reversed. Further, the electrocardiogram signal and the EMG signal may also be simultaneously measured.

In an ultimate process, the determination module 120 may determine muscle fatigue of the cyclist, based on at least one of a change in a heart rate of the measured electrocardiogram signal and a change in a frequency component of the measured EMG signal, in S603.

In detail, as described above, the determination module 120 may determine that fatigue has accumulated in the muscles when the heart rate obtained, based on the electrocardiogram signal, is equal to or greater than a preset threshold value.

Alternatively, the determination module 120 may determine that, when an intermediate frequency 402 obtained, based on the EMG signal, is lower than a first threshold frequency and/or an average frequency 401 obtained, based on the EMG signal, is lower than a preset second threshold frequency, fatigue has accumulated in the muscles.

As described above, according to an exemplary embodiment, as muscle fatigue may be determined, based on ECG and EMG of a cyclist, an accident may be prevented from occurring due to injuries such as cardiac arrest or muscle spasms by excessive exercise.

A method of monitoring a biosignal of a cyclist according to an exemplary embodiment, described above, may be produced as a program to be executed in a computer, and may be stored in a computer-readable recording medium. Examples of the computer-readable recording medium may include a read only memory (ROM), a random access memory (RAM), a CD-ROM, a magnetic tape, a floppy disk, an optical data storage device, and the like. In addition, computer-readable recording media may be distributed in a network-connected computer system, in which computer-readable codes readable in a distributed manner may be stored and may be executed. Functional programs, codes, and code segments for implementations of the method may be easily carried out by programmers in the art.

In addition, in describing exemplary embodiments of the present disclosure, 'module', 'unit' or 'portion' may be implemented in various manners using, for example, a processor, program instructions executed by a processor, a software module, a microcode, a computer program product, a logic circuit, an application-dedicated integrated circuit, firmware, or the like.

As set forth above, according to an exemplary embodiment, by determining muscle fatigue based on electrocardiogram and electromyogram of a cyclist, the occurrence of an accident due to injuries such as cardiac arrest or muscle spasms due to excessive exercise may be prevented.

While exemplary embodiments have been shown and described above, it will be apparent to those skilled in the art that modifications and variations could be made without departing from the scope of the present invention as defined by the appended claims.

What is claimed is:

1. An apparatus for monitoring a biosignal of a cyclist, comprising:
   an electrocardiogram measuring sensor for measuring an electrocardiogram signal of a cyclist;
   an electromyogram measuring sensor for measuring an electromyogram signal of the cyclist; and
   a determination module for determining muscle fatigue of the cyclist, based on the module deriving at least one of a change in a heart rate from the measured electrocardiogram signal and a change in a frequency component from the measured electromyogram signal, wherein the electromyogram measuring sensor comprises:
      a lower electrode including a through hole and configured to be attached to a skin of the cyclist to detect the biosignal;
      an upper electrode provided on one surface of the lower electrode to form a closed space between the upper electrode and the lower electrode and configured to receive the biosignal detected by the lower electrode; and
      an air discharge portion formed in one of the lower electrode and the upper electrode and configured to allow the upper electrode and the lower electrode to be attached to the skin of the cyclist by discharging air present in the closed space and the through hole externally.

2. The apparatus of claim 1, wherein the determination module comprises:
   a fast fourier transform (FFT) conversion unit performing FFT conversion on the measured electromyogram signal;
   an operation unit obtaining at least one of an intermediate frequency and an average frequency of the electromyogram signal having been FFT-transformed; and
   a fatigue determination unit determining that fatigue has accumulated in a muscle when the obtained intermediate frequency is lower than a first threshold frequency, or the obtained average frequency is lower than a preset second threshold frequency.

3. The apparatus of claim 2, wherein the intermediate frequency of the electromyogram signal is a frequency at a point obtained by dividing an area of the electromyogram signal in half, and the average frequency of the electromyogram signal is a frequency at a point representing an average value of the electromyogram signal having been FFT-transformed.

4. The apparatus of claim 2, wherein the fatigue determination unit determines that fatigue has accumulated in the muscle, when the heart rate obtained, based on a QRS wave or a P wave of the measured electrocardiogram signal, is equal to or greater than a preset threshold value.

5. The apparatus of claim 2, wherein the determination module includes a bandpass filter removing a frequency, other than a frequency of a frequency band of the heart rate of the measured electrocardiogram signal and a frequency of a frequency band of the measured electromyogram signal.

6. The apparatus of claim 1, wherein the electrocardiogram measuring sensor includes a dry electrode configured for attachment to a handlebar of a bicycle, and
   the electromyogram measuring sensor is configured for attachment to a thigh of the cyclist.

7. A method of monitoring a biosignal of a cyclist, comprising:
   measuring an electrocardiogram signal of a cyclist by an electrocardiogram measuring sensor;
   measuring an electromyogram signal of the cyclist by an electromyogram measuring sensor; and
   determining a degree of muscle fatigue of the cyclist, by a determination unit, based on the unit deriving at least one of a change in a heart rate from the measured electrocardiogram signal and a change in a frequency component from the measured electromyogram signal, wherein the electromyogram measuring sensor comprises:
      a lower electrode including a through hole and configured to be attached to a skin of the cyclist to detect the biosignal;
      an upper electrode provided on one surface of the lower electrode to form a closed space between the upper electrode and the lower electrode and configured to receive the biosignal detected by the lower electrode; and
      an air discharge portion formed in one of the lower electrode and the upper electrode and configured to allow the upper electrode and the lower electrode to be attached to the skin of the cyclist by discharging air present in the closed space and the through hole externally.

8. The method of claim 7, wherein the third operation comprises:
performing FFT conversion on the electromyogram signal;
obtaining at least one of an intermediate frequency and an average frequency of the electromyogram signal having been FFT-transformed; and
determining that muscle fatigue has accumulated when at least one of the obtained intermediate frequency and the obtained average frequency is lower than a preset threshold frequency.

9. The method of claim 8, wherein the intermediate frequency of the electromyogram signal is a frequency at a point obtained by dividing an area of the electromyogram signal having been FFT-transformed, in half, and the average frequency of the electromyogram signal is a frequency at a point representing an average value of the electromyogram signal having been FFT-transformed.

10. The method of claim 9, wherein the third operation comprises determining that fatigue has accumulated in a muscle when the heart rate obtained, based on a QRS wave or a P wave of the measured electrocardiogram signal, is equal to or greater than a preset threshold value.

11. The method of claim 8, further comprising removing a frequency, other than a frequency of a frequency band of the heart rate of the measured electrocardiogram signal and a frequency of a frequency band of the measured electromyogram signal.

12. The method of claim 7, wherein measuring an electrocardiogram signal includes attaching a dry electrode of the electrocardiogram measuring sensor to a handlebar of a bicycle, and
measuring an electromyogram signal includes attaching the electromyogram measuring sensor to a thigh of the cyclist.

13. A non-transitory recording medium including a program to perform the method of claim 7.

* * * * *